United States Patent [19]

Suzuki et al.

[11] Patent Number: 4,480,033

[45] Date of Patent: Oct. 30, 1984

[54] LANKACIDINS PRODUCTION

[75] Inventors: Takashi Suzuki, Takatsuki; Junya Okada, Hirakata; Hidekazu Sawada, Neyagawa, all of Japan

[73] Assignee: Takeda Chemical Industries, Ltd., Osaka, Japan

[21] Appl. No.: 482,552

[22] Filed: Apr. 6, 1983

[30] Foreign Application Priority Data

Apr. 12, 1982 [JP] Japan ................................. 57-61342

[51] Int. Cl.³ ...................... C12P 17/08; C12P 13/02; C12R 1/465

[52] U.S. Cl. .................................. 435/124; 435/129; 435/886

[58] Field of Search ............................... 435/124, 129

[56] References Cited

U.S. PATENT DOCUMENTS 3,188,272 6/1965 Gottlieb et al. ..................... 424/121
3,626,055 7/1971 Higashide et al. .................. 424/120
3,691,181 9/1972 Kishi et al. ..................... 424/283 X

OTHER PUBLICATIONS

Chemical Abstracts, vol. 96, 223,270w (1982).
Chemical Abstracts, vol. 95, 78,368g (1982).
Chemical Abstracts, vol. 98, 124208s (1983).
Uramoto et al., Agricultural and Biological Chemistry, vol. 35, No. 1, pp. 27–32 (1971).

Primary Examiner—Lionel M. Shapiro
Attorney, Agent, or Firm—Wenderoth, Lind & Ponack

[57] ABSTRACT

Yield of lankacidin antibiotics is enhanced by incorporating cyclodextrin into a culture medium where a microorganism capable of producing lankacidin is cultivated.

6 Claims, No Drawings

LANKACIDINS PRODUCTION

The present invention relates to an improved process for producing lankacidins.

The term "lankacidins" is the name of a group of antibiotics represented by the following formulae (I) and (II), including such structurally unidentified antibiotics as lankacidin K and lankacidin L:

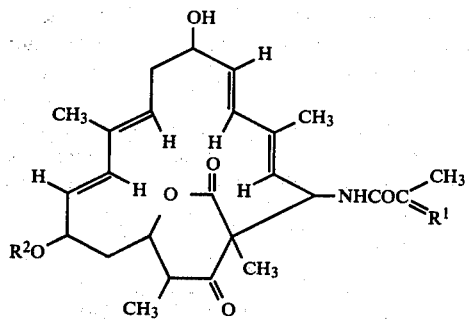

wherein $R^1$ is =O, or —H and —OH, and $R^2$ is hydrogen or lower alkanoyl,

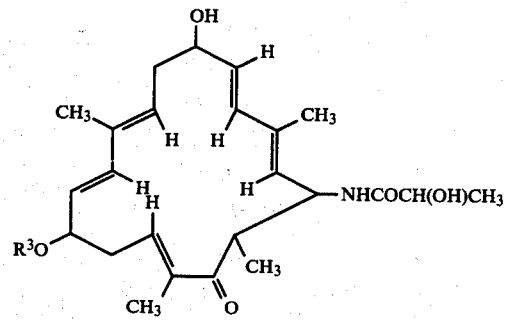

wherein $R^3$ is hydrogen or lower alkanoyl. Those lankacidins are otherwise designated as antibiotic T-2636. There are, for example, lankacidin A (I; $R^1$: =O, $R^2$: $COCH_3$), lankacidin C (I; $R^1$: =O, $R^2$: H), lankacidinol A

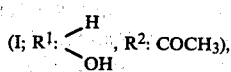

lankacidinol

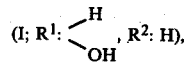

lankacyclinol (II; $R^3$: H), lankacyclinol A (II; $R^3$: $COCH_3$), and said structurally unidentified lankacidins K and L.

The physico-chemical and biological properties of lankacidins of the formulae (I) and (II) have been known [The Journal of Antibiotics, Vol. 24, 1, (1971); ibid., Vol. 26, 647 (1973); Chemical Pharmaceutical Bulletin, Vol. 22, 99, (1974); ibid., Vol. 23, 2201 (1975)], while the physico-chemical and biological properties of the lankacidins K and L are disclosed in Japanese Patent Application No. 150018/1981 filed on Sept. 22, 1981.

A considerable progress of the study on uses of the lankacidins has been made, and it has recently been revealed that they are effective as antibacterial and antitumor agents. It is expected that demand of the lankacidins will increase more and more especially because of their remarkably low toxicities.

Under the foregoing situation, the present inventors have studied for establishing a process of producing lankacidins on a large scale at a low cost to reach the method of this invention.

According to the present invention, culturing a microorganism capable of producing the lankacidins in a culturing medium is carried out in the presence of a cyclodextrin.

Any microorganism capable of producing the lankacidins can be used, but those belonging to the genus Streptomyces (hereinafter referred to as "St.") are preferable. Examples of such microorganisms are *St. rochei* var. *volubilis* (IFO-12507; ATCC-21250; FERM P-6155; U.S. Pat. No. 3,626,055), *St. griseofuscus* [IFO-12870; ATCC-23916; ATCC Catalogue of Strains I (14th. ed., 1980), p 175]. *St. violaceoniger* (NRRL-2834; IFO-14166; U.S. Pat. No. 3,118,812), and *St.* sp. 6642-GC₁, [IFO-14172; Agr. Biol., Chem. 35(1), 27–32 (1971)].

Cyclodextrins used in the process are α-cyclodextrin, β-cyclodextrin, γ-cyclodextrin and δ-cyclodextrin. These cyclodextrins may be used alone or in combination of the two or more, for example, a mixture of β-cyclodextrin and γ-cyclodextrin may be used.

Concentration of cyclodextrin in a culture medium is not critical so long as it does not inhibit growth of the microorganisms, but usually between 1–150 mM, preferably, 2–100 mM, more particularly 4–50 mM.

Cyclodextrins may be in the crystalline, powder or liquid form or may contain impurities, such as sugar or starch. Amount of such impure cyclodextrins, when they are used, is so controlled that net concentration of the cyclodextrin falls within the above mentioned range.

Addition of cyclodextrins to the culture medium may be made at any time of the culturing, but preferably before the microorganism is inoculated or transplanted to the medium.

Carbon sources of the culturing medium are, for instance, not only saccharides such as starch, dextrin, glucose, maltose, sucrose, sorbitol, molasses, corn syrup or millet jelly but also organic acids such as acetic acid or succinic acid, polyhydric alcohols such as glycerol, fats and oils. Nitrogen sources are inorganic substances such as ammonium salts, nitrates or urea and natural organic substances such as yeast extract, casein, meat extract, cotton seed draff, corn steep liquor and soybean draff. In addition, there are used, if necessary, inorganic salts such as iron (e.g., ferrous sulfate), magnesium (e.g., magnesium sulfate), manganese (e.g., manganese sulfate), cobalt (e.g., cobalt sulfate), copper (e.g., copper sulfate), sodium (e.g., sodium chloride), potassium (e.g., potassium carbonate), calcium (e.g., calcium carbonate), zinc (e.g., zinc chloride) and the like. Furthermore, there may be used amino acids, vitamins or nucleic acid bases when the microorganism employed demands.

Any of stationary, aeration-agitation or shaking culture may be used, but preferably aeration-agitation culture. Culturing is conducted at a temperature of 15° C. to 40° C., preferably 20° C. to 34° C. The pH of the culture medium is preferably within a range of 4 to 9. To this effect, sodium hydroxide, potassium hydroxide, aqueous ammonia, or a dilute aqueous solution of sulfuric acid or hydrochloric acid is added to control the pH value during the culturing. Alternatively, alkali salts such as potassium carbonate or sodium carbonate may be added to the culturing medium. Culturing is made until a substantial amount of lankacidin is accumulated, but usually for 2 to 12 days in order to obtain the maximum yield.

The lankacidins accumulated in the culture broth can be isolated by conventional techniques conventionally used therefor. For example, extraction is made from the culture broth or its filtrate with a water-insoluble solvent such as ketones (e.g., acetone, 4-methyl-2-pentanone), esters (e.g., ethyl acetate, ethyl propionate) or hydrocarbons (e.g., hexane, benzene), by taking advantage of their properties that they are neutral and lipophilic. The extract is washed with an aqueous acid solution and an aqueous alkali solution and evaporated to give the crude lankacidin. The crude product can be further purified by column chromatography on silica gel, alumina or the like according to the known method disclosed in the publications mentioned before, if necessary. Lankacidins thus obtained can further be individually separated into their constituents.

The hydroxy group at the 14-position of the lankacidin can selectively be changed to the corresponding esters by adding to said culture broth, preferably its filtrate esters such as $C_{1-4}$ alcohol esters, glycol esters or glycerol esters of lower ($C_1$-$C_5$) alkylcarboxylic acids, e.g., acetic acid, propionic acid. Examples of the esters are methyl formate, ethyl acetate, ethyl propionate, monoacetin and triacetin. The hydroxy group at the 14-position is esterified by the enzyme in the culture broth, for example, by adding ethyl acetate to the culture broth to give the corresponding 14-acetyl ester derivative. The esterification is carried out, for example, by adding an ester to a filtrate of the culture broth in an amount of ¼-2 times as much as the filtrate, and stirring the mixture until it is emulsified, usually for 1 minute to 1 hour, at a temperature of 15° C. to 70° C., preferably 20° C. to 40° C., under pH 4 to 9. The 14-ester derivatives prepared as above can be isolated from the reaction mixture in the same method as mentioned above.

The lankacidins prepared as above can be used as antitumor agents, antibacterial agents and antibiotic for swine dysentery.

The following examples are given to illustrate the present invention more precisely, but they should not be construed to limit the scope of the present invention.

In the following examples, percentages are by weight per volume unless otherwise indicated.

EXAMPLE 1

(1) 25 ml of a culture medium containing soluble starch (1%), raw soybean flour (2%), calcium carbonate (1%) and soybean oil (0.1%) was put in a 200 ml flask and sterilized. The medium was inoculated with one loop of plant culture of Streptomyces rochei var. volubilis (IFO-12507) and incubated at 28° C. on a rotary shaker at 200 rpm for 24 hours. This was used as a seed culture.

To 25 ml each of a culture medium containing glycerol (10%), Proflo(Traders Oil Mill Co., U.S.A.) (2%), corn steep liquor (0.5%), Polypepton (Daigo Nutritive Chemicals, Ltd., Japan) (1%), ferrous sulfate (0.1%), and soybean oil (0.01%) was added β-cyclodextrin until concentration of the β-cyclodextrin in the resulting culture medium was shown in Table 1. The pH values of the mixtures were controlled to 7.0 by adding 20% aqueous solution of sodium hydroxide.

20 ml each of the mixtures was placed in a 200 ml flask, and sterilized. These media were inoculated with 1 ml of the seed culture, and incubated at 24° C. on a rotary shaker at 200 rpm for 96 hours. The lankacidins accumulated in the culture broths were quantitatively determined by a known method [The Journal of Antibiotics, Vol. 24, 1 (1971)]. Namely, the amounts were calculated from bioassays of the samples as follows:

Lankacidin prepared as above was extracted with methyl isobutyl ketone. The extract was developed on a thin layer chromatography (spot film, by Tokyo Kasei Co., Japan) with a mixture of ethyl acetate and ethyl ether (1:3). Diameter of the inhibition zone against the growth of Sarcina lutea PCI-1001 was compared with that of the standard.

The results are given in Table 1.

TABLE 1

| Concentration of β-cyclodextrin (mM) in the culture medium | Lankacidin C (mM) | Lankacidin A (mM) |
|---|---|---|
| 0 | 0.40 | 0.05 |
| 1 | 0.60 | 0.07 |
| 3 | 1.74 | 0.19 |
| 5 | 4.00 | 0.44 |
| 7 | 4.00 | 0.52 |
| 9 | 4.20 | 0.53 |
| 11 | 4.60 | 0.55 |
| 30 | 4.50 | 0.55 |
| 50 | 4.52 | 0.55 |

(2) One liter of the culture broth obtained in above wherein 9 mM of β-cyclodextrin was added was centrifuged. The supernatant liquid was extracted with 4-methyl-2-pentanone (1 l), washed with water and evaporated under reduced pressure. To the concentrate, was added 100 ml of n-hexane to give 3 g of precipitates. 2.5 g of the crude substance thus obtained was dissolved in 25 ml of a mixed solvent of chloroform and ethyl acetate (1:1), which was subjected to adsorption chromatography on 75 g of silica gel (0.05-0.2 mm: Merck & Co., U.S.A.).

After ether (250 ml) was passed through the column, elution was made with a 1:1 mixture of ether and ethyl acetate (1 l), ethyl acetate (1 l) and a 1:1 mixture of ethyl acetate and acetone (1 l), successively, thereby most of the antibacterially effective fractions were contained in the eluates.

Effective fractions were pooled and concentrated to give about 1.4 g of yellow powder. This crude powder was subjected to thin layer chromatography on 0.5 kg of silica gel (HF254: Merck & Co., U.S.A.). The crude product was separated into the respective antibiotics constituting the lankacidin-group antibiotics.

The chromatogram was developed with a mixed solvent of ethyl acetate and ether (1:3), and extracted with ethyl acetate. After washing with water, the extracts were dried, concentrated and then recrystallized, respectively, to give 40 mg of lankacidin C and 3.5 mg of lankacidin A.

Their melting points, specific rotations (c=1.0, ethanol), ultraviolet absorptivities (at 227 nm), and elementary analysis were exactly identical to the values disclosed in the publication [The Journal of Antibiotics, Vol. 24, 13 (1971)].

EXAMPLE 2

To 25 ml each of a culture medium containing glucose (5%), glycerol (0.5%), Polypepton (1%), meat extract (0.5%), raw soybean flour (1%), magnesium sulfate (0.1%) and potassium carbonate (0.5%) in a 200 ml flask, was added β-cyclodextrin until concentrations as in Table 2 were attained and sterilized.

To each of the culture media, was put 1 ml of the seed culture of *Streptomyces rochei* var. *volubilis* (IFO-12507) obtained in Example 1. Culturing was made at 24° C. on a rotary shaker at 200 rpm for 96 hours. Amount of each lankacidin accumulated in each of the culture broths was measured according to the same method as that of Example 1.

TABLE 2

| Concentration of β-cyclodextrin added (mM) | Lankacidinol (mM) | Lankacidinol A (mM) | Lankacyclinol A (mM) |
|---|---|---|---|
| 0 | 0.21 | 0.04 | 0.13 |
| 1 | 0.32 | 0.06 | 0.19 |
| 3 | 1.23 | 0.16 | 0.55 |
| 5 | 2.80 | 0.39 | 1.40 |
| 7 | 2.85 | 0.41 | 1.42 |
| 9 | 2.91 | 0.41 | 1.40 |
| 11 | 2.91 | 0.42 | 1.39 |
| 30 | 2.89 | 0.40 | 1.41 |
| 50 | 2.88 | 0.40 | 1.40 |

EXAMPLE 3

Example 1, (1) was repeated except that various cyclodextrins, alone or a mixture thereof, were used in such amounts as in the Table 3 in place of the β-cyclodextrin. The amounts of the products were measured by the same method as that of Example 1, (1).

The results are given in Table 3.

TABLE 3

| Concentration of cyclodextrin added | | Lankacidin C (mM) | Lankacidin A (mM) |
|---|---|---|---|
| β-cyclodextrin | 10 mM | 4.40 | 0.54 |
| α-cyclodextrin | 10 mM | 0.75 | 0.08 |
| γ-cyclodextrin | 10 mM | 3.01 | 0.35 |
| β-cyclodextrin | 5 mM | 4.10 | 0.49 |
| α-cyclodextrin | 5 mM | | |
| β-cyclodextrin | 5 mM | 4.25 | 0.51 |
| γ-cyclodextrin | 5 mM | | |
| α-cyclodextrin | 5 mM | 3.21 | 0.40 |
| γ-cyclodextrin | 5 mM | | |
| α-cyclodextrin | 3 mM | 3.02 | 0.38 |
| β-cyclodextrin | 3 mM | | |
| γ-cyclodextrin | 3 mM | | |
| None | | 0.40 | 0.05 |

EXAMPLE 4

25 ml each of a culture medium containing soluble starch (2.8%), raw peanut flour (3.0%), molasses (0.5%), Polypepton (0.5%), calcium carbonate (0.3%), sodium chloride (0.25%), zinc sulfate (0.003%), copper sulfate (0.0007%), manganese sulfate (0.0007%), and soybean oil (0.2%) was put in a 200 ml flask and sterilized. This medium was inoculated with one loop of slant culture of *Streptomyces griseofuscus* IFO-12870 and incubated on a rotary shaker at 200 rpm at 28° C. for 30 hours. This was used as a seed culture.

To 25 ml each of a culture medium having the same composition as above, cyclodextrins indicated in Table 4 were added in the amount indicated in the same Table. These mixtures were put in 200 ml flasks, respectively, and sterilized.

One mililiter of the above mentioned seed culture was transplanted to each of the mixtures and the mixtures were incubated on a rotary shaker at 200 rpm at 24° C. for 96 hours. Lankacidins accumulated in the culture media were measured in the same manner as that of Example 1, (1).

The results are given in Table 4.

TABLE 4

| Concentration of cyclodextrin added | | Lankacidin C (mM) | Lankacidin A (mM) |
|---|---|---|---|
| β-cyclodextrin | 10 mM | 1.55 | 0.21 |
| α-cyclodextrin | 10 mM | 0.31 | 0.04 |
| γ-cyclodextrin | 10 mM | 1.10 | 0.12 |
| β-cyclodextrin | 5 mM | 1.50 | 0.19 |
| α-cyclodextrin | 5 mM | | |
| β-cyclodextrin | 5 mM | 1.53 | 0.20 |
| γ-cyclodextrin | 5 mM | | |
| α-cyclodextrin | 5 mM | 1.12 | 0.13 |
| γ-cyclodextrin | 5 mM | | |
| α-cyclodextrin | 3 mM | 1.11 | 0.13 |
| β-cyclodextrin | 3 mM | | |
| γ-cyclodextrin | 3 mM | | |
| None | | 0.15 | 0.02 |

EXAMPLE 5

500 ml of a culture medium containing glucose (3%), Proflo (1%), corn steep liquor (3.5%), magnesium sulfate (0.02%), dipotassium hydrogen phosphate (0.1%), soybean oil (0.05%), and calcium carbonate (1.5%) was controlled to pH 7.0 with a 20% aqueous sodium hydroxide solution. The culture medium was put in a 2 liter Sakaguchi-flask and sterilized after plugged with cotton. The culture medium was then inoculated with a slant culture of *Streptomyces rochei* var. *volubilis* IFO-12507 and incubated on a reciprocal shaker at 28° C. for 24 hours. 30 liters of a culture medium of the same composition as above was placed in a 50 liter fermenter and sterilized. 500 ml of the above mentioned culture broth was inoculated into the above culture medium and incubated at 24° C. for 24 hours with aeration of 1 VVM (aeration volume per minute per volume of the medium) and stirring at 150 rpm. This was used as a seed culture. In a 200 liter fermenter, 100 liters of a culture medium containing glycerol (10%), Proflo (2%), corn steep liquor (0.5%), Polypepton (1%), ferrous sulfate (0.1%), soybean oil (0.1%), and β-cyclodextrin (1%) was placed and sterilized. To this culture medium, 5 liters of the above mentioned seed culture was transplanted and incubated at 24° C. for 96 hours with the aeration of 1 VVM and stirring at 165 rpm.

To 60 liters of the culture broth thus obtained, were added 20 liters of water and 2 kg of Hyflo-Supercel (Johns Manville Products Corp., U.S.A.) and the mixture was filtered to give 70 liters of filtrate. A part of the filtrate was subjected to lankacidin assay to find 3.3 mM of lankacidin C and 0.2 mM of lankacidin A. 70 liters of the filtrate was put in a 200 l vessel equipped with a stirrer. After 35 l of ethyl acetate was added to the filtrate, the filtrate was stirred for 30 minutes at room temperature with a stirrer rotating at 120 rpm, and a part of the filtrate was sampled to determine contents of lankacidins. Lankacidin C was not found in the sample, but Lankacidin A was found in it. After the filtrate was stirred for 1 hour with ethyl acetate, the ethyl acetate layer was isolated and concentrated to 5 l with a rotary evaporator (inner temperature: 30° C.). This concentrate was subjected to adsorption chromatography on 10 kg of the silica gel (0.05 mm–0.2 mm, Merck & Co., U.S.A.) equilibrated with toluene. The column was eluted with 30 l of toluene and then 120 l of a mixed solvent of toluene and ethyl acetate (8:2). One liter aliquot each of the eluate was fractionally collected and the active fractions were evaporated with a rotary evaporator (inner temperature 30° C.) to precipitate crystals. The crystals were dried to yield 80.0 g of crystalline lankacidin A.

EXAMPLE 6

A 20% aqueous sodium hydroxide solution was added drop by drop to a culture medium containing glucose (3%), Proflo (1%), corn steep liquor (3.5%), magnesium sulfate (0.02%), dipotassium hydrogen phosphate (0.1%) and calcium carbonate (1.5%) to control pH value of the culture medium to 6.5. 25 ml of this culture medium was put in a 200 ml Erlenmeyer flask, plugged with cotton and sterilized. The culture medium was inoculated with one loop of a slant culture of *Streptomyces violaceoniger* (IFO-14166), and incubated at 28° C. for 24 hours on a rotary shaker at 200 rpm. This culture broth was used as a seed culture. To culture media containing glycerol (10%), Proflo (2%), corn steep liquor (0.5%), Polypepton (1%), ferrous sulfate (0.1%), copper sulfate (0.0025%) and sodium chloride (0.5%), was added β-cyclodextrin in the amounts indicated in Table 5. The pH of the mixture were adjusted to 6.0 by adding dropwise a 20% aqueous sodium hydroxide solution. 25 ml each of the medium was placed in 200 ml Erlenmeyer flasks and sterilized at 120° C. for 20 minutes. These culture media were inoculated with 1 ml of the seed culture, and incubated at 24° C. for 96 hours on a rotary shaker at 200 rpm. The amounts of lankacidins accumulated in the culture media were measured by the same method as that of Example 1. The results are given in Table 5.

TABLE 5

| Concentration of β-cyclodextrin in a culture medium (mM) | Lankacidin C (mM) | Lankacidinol (mM) |
|---|---|---|
| 0 | 0.40 | 0.06 |
| 2.25 | 2.55 | 0.78 |
| 4.5 | 3.76 | 0.80 |
| 9 | 4.60 | 1.25 |
| 13.5 | 4.04 | 2.33 |
| 18 | 4.01 | 2.66 |

EXAMPLE 7

10 ml of the culture broth of Example 6, of which concentration of β-cyclodextrin in the culture medium was 9 mM as given in Table 5, was centrifuged at room temperature at 2000 rpm. 6 ml of the supernatant was put in a 100 ml Erlenmeyer flask equipped with a stopper and 6 ml of ethyl acetate was added thereto. The mixture was agitated at 18° C. for 30 minutes at 200 rpm so that acetylation reaction took place. After the ethyl acetate layer was separated with a 50 ml separatory funnel, contents of lankacidins were measured by the same method as that of Example 1. The results are given in Table 6.

TABLE 6

| Lankacidins | Concentration of the reaction product (mM) |
|---|---|
| Lankacidin A | 4.55 |
| Lankacidinol A | 1.21 |

EXAMPLE 8

Cultivation was conducted in the same manner as that of Example 6 except that *Streptomyces* sp. 6642-GC$_1$ (IFO-14172) was used instead of *Streptomyces violaceoniger* (IFO-14166). Contents of lankacidins accumulated in the culture broths were measured by the same method as that of Example 1. The results are given in Table 7.

TABLE 7

| Concentration of β-cyclodextrin in the culture medium (mM) | Lankacidin C (mM) | Lankacidinol (mM) |
|---|---|---|
| 0 | 0.39 | 0.037 |
| 2.25 | 0.68 | 0.101 |
| 4.5 | 0.79 | 0.135 |
| 9 | 0.59 | 0.060 |
| 13.5 | 0.54 | 0.051 |
| 18 | 0.54 | 0.050 |

EXAMPLE 9

10 ml of the culture broth prepared in the experiment of Example 8 wherein concentration of β-cyclodextrin in the culture medium was 4.5 mM as given in Table 7 was subjected to acetylation reaction in the same procedure as that of Example 7.

The results are given in Table 8.

TABLE 8

| Lankacidins | Concentration of the reaction product (mM) |
|---|---|
| Lankacidin A | 0.75 |
| Lankacidinol A | 0.138 |

What is claimed is:

1. A method for improving production of lankacidin antibiotics by culturing a microorganism capable of producing lankacidin, wherein cyclodextrin is added in a culture medium.

2. A method according to claim 1, wherein said cyclodextrin is added to the culture medium before the microorganism is innoculated or transplanted to the culture medium, and the concentration of the cyclodextrin in the medium is between 1–150 mM.

3. A method according to claim 1, wherein said microorganism is *Streptomyces rochei* var. *volubilis* (ATCC-21250), *Streptomyces griseofuscus* (ATCC-23916), *Streptomyces violaceoniger* (IFO-14166) or *Streptomyces* sp. 6642-GC$_1$, (IFO-14172).

4. A method for producing lankacidin 14-acyl derivative or a mixture containing mainly the same which comprises culturing a microorganism capable of producing lankacidin in a culture medium containing a cyclodextrin and adding a lower alkylcarboxylate to the resulting culture broth or filtrate thereof, whereby to effect esterification.

5. A method according to claim 4, wherein the lower alkylcarboxylate is ethyl acetate and the lankacidin 14-acyl derivative or the mixture containing mainly the same is 14-acetyl derivative of lankacidin C or a mixture containing mainly the same.

6. A method according to claim 5, wherein *Streptomyces rochei* var. *volubilis* (ATCC-21250) is microorganism to be cultivated.

* * * * *